(12) United States Patent
Xu et al.

(10) Patent No.: US 7,899,506 B2
(45) Date of Patent: Mar. 1, 2011

(54) COMPOSITE SPECTRAL MEASUREMENT METHOD AND ITS SPECTRAL DETECTION INSTRUMENT

(75) Inventors: Kexin Xu, Tianjin (CN); Yiwen Ma, Tianjin University (CN); Renda Wang, Tianjin (CN)

(73) Assignee: Tianjin Sunshine Optics Technolies Co. Ltd., Tianjin (CN)

( * ) Notice: Subject to any disclaimer, the term of this patent is extended or adjusted under 35 U.S.C. 154(b) by 1330 days.

(21) Appl. No.: 10/532,669

(22) PCT Filed: Sep. 25, 2003

(86) PCT No.: PCT/CN03/00820

§ 371 (c)(1),
(2), (4) Date: Dec. 12, 2005

(87) PCT Pub. No.: WO2004/046696

PCT Pub. Date: Jun. 3, 2004

(65) Prior Publication Data

US 2006/0167347 A1    Jul. 27, 2006

(30) Foreign Application Priority Data

Nov. 4, 2002    (CN)    ................................ 02 1 46704

(51) Int. Cl.
*A61B 5/1455* (2006.01)
(52) U.S. Cl. .................. 600/316; 600/310; 600/473
(58) Field of Classification Search .......... 600/309–344
See application file for complete search history.

(56) References Cited

U.S. PATENT DOCUMENTS 4,655,225 A * 4/1987 Dahne et al. ................. 600/316
5,028,787 A     7/1991 Rosenthal et al.
5,267,152 A     11/1993 Yang et al.
5,348,003 A *  9/1994 Caro ........................... 600/310
5,746,697 A *  5/1998 Swedlow et al. ............ 600/323
5,974,337 A     10/1999 Kaffka et al.
5,999,081 A * 12/1999 Hannigan et al. ............. 338/28

(Continued)

FOREIGN PATENT DOCUMENTS

CN    1051297 A    5/1991

(Continued)

*Primary Examiner* — Eric F Winakur
(74) *Attorney, Agent, or Firm* — McDermott Will & Emery LLP

(57) ABSTRACT

The present invention discloses a spectral measurement method via continuous light source and discrete light source, and a measurement instrument for non-invasive detection of human body tissue components. Said instrument includes an incident unit, a probe, a receiving unit and a data processing unit. Said composite spectral measurement method improves or strengthens the output light intensity at the wavelength that carries information of the target component within human body. It enables the spectral detection in the whole wavelength range, and thus significantly enhances the SNR of the detecting system. In the non-invasive detection instrument, light from both the continuous light source and discrete light source can be firstly selectively light-split by AOTF, or AOTF conducts light-splitting for the continuous light source, while the discrete light source LD is controlled by a spatial chopper. When data of the spectral curves achieved from said continuous light source and discrete light source are processed, data acquired under different measuring modes can be compared.

17 Claims, 13 Drawing Sheets

U.S. PATENT DOCUMENTS

| | | | |
|---|---|---|---|
| 6,070,093 A | 5/2000 | Oosta et al. | |
| 6,172,743 B1 | 1/2001 | Kley et al. | |
| 6,678,541 B1 * | 1/2004 | Durkin et al. | 600/310 |
| 6,741,876 B1 | 5/2004 | Scecina et al. | |
| 6,990,364 B2 * | 1/2006 | Ruchti et al. | 600/310 |
| 7,133,710 B2 * | 11/2006 | Acosta et al. | 600/316 |
| 7,299,079 B2 * | 11/2007 | Rebec et al. | 600/316 |
| 7,317,938 B2 * | 1/2008 | Lorenz et al. | 600/316 |
| 2006/0184040 A1 * | 8/2006 | Keller et al. | 600/476 |

FOREIGN PATENT DOCUMENTS

| | | |
|---|---|---|
| EP | 0250070 A1 | 12/1987 |
| EP | 0426358 A1 | 5/1991 |
| EP | 0694769 A1 | 1/1996 |
| JP | 02-018851 | 1/1990 |
| JP | 8-27235 A | 1/1996 |
| JP | 2588468 | 10/1998 |
| WO | WO 90/07905 A1 | 7/1990 |
| WO | WO 96/07889 A1 | 3/1996 |
| WO | WO 01/16577 A1 * | 3/2001 |

* cited by examiner

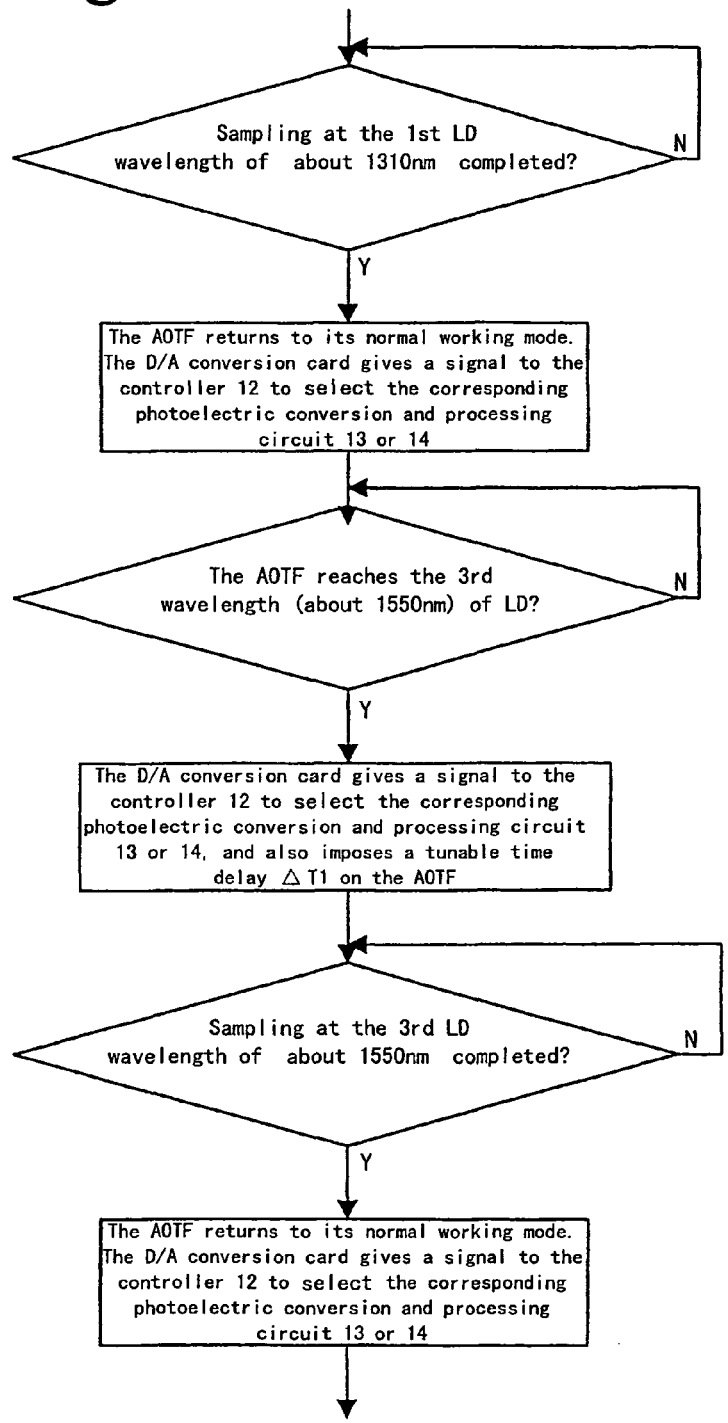

COMPOSITE SPECTRAL MEASUREMENT METHOD AND ITS SPECTRAL DETECTION INSTRUMENT

This application is a U.S. national filing under 35 U.S.C. 371 and claims priority from PCT/CN2003/000820, filed 25 Sep. 2003, and from 02146704.8-Filed: 4 Nov. 2002 (each incorporated by reference herein).

FIELD OF THE INVENTION

The present invention relates to a detection method and instrument, more particularly to a method and instrument for composite spectral measurement via a composite light source.

BACKGROUND OF THE INVENTION

Non-invasive detection of the concentration of a certain component within a substance especially human tissue represents great importance in clinical medicine, and in particular, non-invasive detection of the concentration of blood glucose within human body plays a key role in diabetic diagnosis. Till now some related non-invasive detection instruments have been successfully developed by some research institutions in Japan, USA and Western Germany, etc. For most of these non-invasive detection instruments, NIR spectroscopy is applied, wherein because different components within a substance especially human tissue possess different light absorption coefficients in NIR range, the concentration of one or several target components can be detected through analyzing the measured absorption spectra. U.S. Pat. No. 5,348,003 is an example introducing a method and instrument using continuous spectra for non-invasive detection of the concentration of multiple components in a substance; in U.S. Pat. No. 5,028,787, a method and instrument for non-invasively detecting blood glucose concentration through analyzing continuous spectra is presented; in Japanese Registered Utility Model Applications NO. 2588468, an LED with its wavelength ranging from 1.4 to 1.7 μm is used as a light source for non-invasive detection; in Japan Patent Publication No. 8-27235, a setup for chemical analysis is presented using single-wavelength laser. In all these non-invasive detection methods or instruments, a continuous light source or discrete light source is used to create NIR spectra, whereas none of those instruments produce NIR spectra via a composite light source combining continuous light source with discrete light source.

Because generally the absorption wavelength ranges of different components within a substance especially human body overlap, when detection is conducted using a discrete light source that emits single-wavelength light, only overlapped biological information at certain wavelength can be obtained, while information at other wavelengths is very difficult to get. This means, to make a stable and quantitatively non-invasive detecting system, it is a must to achieve high sensitivity, high precision and good accuracy in a considerably broad spectral range, and thus measurement can not take place at a discrete spectrum of a single wavelength or a specific frequency. Firstly, spectra under multiple wavelengths should be obtained. Then by stoichiometric modeling method, the concentration of components of interest can be calculated. In this multiple wavelength spectral measurement, a continuous light source comprises of, for example, a halogen lamp and a light-splitting system, or wavelength tunable laser, or several discrete wavelength LDs, or an interference filter. However, there are not so many LDs, and therefore corresponding products do not exit at each wavelength. Furthermore, each filter has a fixed wavelength. To satisfy the requirement for each wavelength, a considerable number of filters should be used, making the cost of the whole system very high. This is why the method using continuous light source is often appreciated. Consider that the wavelength range is still limited even after the continuous light source passing a light-splitting system and that, because multiple target components within the substance demonstrates strong absorption toward the spectra, e.g., in blood glucose concentration detection, water has great absorption toward NIR spectra, or because the energy of the spectra of the continuous light source is relatively low, the energy of NIR spectra is not enough for the measurement, and in particular, the spectra of the continuous light source may lack some certain NIR spectra that are sensitive to the target components. All these factors obviously make useful information of target components (e.g., blood glucose) that the absorption spectra carry become weaker and directly influence the accuracy, stability and SNR of the detecting system, and thus, it is necessary to introduce one or several discrete light sources plus the continuous light source to form a composite light source, and by the combination of spectra measured by different light sources, composite spectra with high accuracy can be achieved to realize non-invasive detection.

The accuracy of current non-invasive detectors can not meet clinical application requirement, mainly because it is difficult to simultaneously achieve high energy at both multiple wavelengths and at each wavelength in the detecting system. However, through utilizing composite spectra achieved by a composite light source both multiple wavelengths and high energy can be obtained, so that the SNR of the quantitatively non-invasive detecting system can be enhanced, and non-invasive detection of the concentration can be realized.

SUMMARY OF THE INVENTION

The object of the present invention is to provide a spectral measurement method and instrument via a composite light source, a method and instrument for detecting the concentration of components that features spectral measurement through a composite light source, in particular an instrument for non-invasively detecting the concentration of certain component, e.g., blood glucose concentration.

Considering that the absorption wavelength ranges of different components within a substance especially human body overlap intricately, we firstly use a continuous light source that represents continuous spectra in a wide wavelength range for non-invasive detection. In some specific wavelength ranges of the continuous light source spectra, because multiple target components within the substance demonstrates strong absorption toward the spectra, e.g., in blood glucose concentration detection, water has great absorption toward NIR spectra, or because the energy of the spectra of the continuous light source is relatively low, the energy of NIR spectra is not enough for the measurement, and in particular, the spectra of the continuous light source may lack some certain NIR spectra that are sensitive to the target components. All these factors obviously make useful information of target components (e.g., blood glucose) that the absorption spectra carry become weaker and directly influence the accuracy, stability and SNR of the detecting system, and thus, within the continuous light source spectral range or, otherwise, in a NIR spectral range that is sensitive to target components, we introduce one or several discrete light sources as a supplement of the continuous light source.

The present invention is realized by the following aspects.

It is achieved through an incident unit, a probe, a receiving unit and a data processing unit, wherein, the incident unit is composed of the light source of the present invention; the probe is mainly composed of the optical sampling part of the present invention; the receiving unit is mainly composed of the composite spectral method of the present invention; the data processing unit mainly performs mathematical calculation for the composite spectra achieved by the receiving unit so that the concentration of a certain target component such as blood glucose, can be obtained.

The incident unit mainly consists of a light source for creating spectra and an optical setup for light propagation, wherein the composite light source is made up of a continuous light source and a discrete light source.

It mainly consists of a continuous light source with its light-splitting system and at least one discrete light source at a single wavelength such as LD, or at least one narrow-band continuous light source such as LED, or at least one discrete light source at a single wavelength plus at least one narrow-band continuous light source, for instance, LD plus LED.

Presently, instruments for creating continuous NIR spectra generally include Fourier transform NIR spectrometer, raster scanning NIR spectrometer and acoustic optical tunable filter (short as AOTF) NIR spectrometer, etc. A Fourier transform NIR spectrometer can simultaneously measure signals at all wavelengths with a very high SNR and resolution, and the stability of the system is preferable; however, it is expensive and complicated, and presents a strict requirement for the usage and the environment, so it is generally used inside a lab. A raster scanning NIR spectrometer can perform scanning within the whole wavelength range, also with a high resolution; besides, the price is moderate and acceptable, but there is deficiency in the precision, wavelength range, reproducibility and shock resistance. In an AOTF NIR spectrometer, AOTF is used as a light-splitting system. AOTF can perform wavelength switch in a very quick way, with good reproducibility and great flexibility, but its output spectral energy is relatively low. In the present invention, we use AOTF NIR spectrometer as a continuous light source, and simultaneously, to compensate for the low SNR due to its low output spectral energy, we add a set of discrete light sources as complementary light source. Such a structure can enable a setup that is of good performance, with low cost and unlimited using environment.

In practical measurement, an AOTF NIR spectrometer can be used as the continuous light source, while a light source that is able to select and control wavelength can be used as the discrete light source.

Generally, a discrete light source can be a light-emitting diode (LED), a laser diode (LD), or an AOTF, etc. In the present invention one or several LDs are used as the discrete light source. LD has good monochromaticity and centralized light energy.

Through using spectra from one or several LDs in the non-invasive detection of certain components within human tissue, accurate biological information at related wavelength can be obtained In this spectral measurement method via a composite light source comprising of a continuous light source and a discrete light source, light from the continuous light source and discrete light source can be first light-split by AOTF selectively, then irradiates on the target skin after passing corollary equipment such as a fiber. Light propagation can also take place in the follow way: AOTF conducts light-splitting for the continuous light source, while the discrete light source LD is controlled by a spatial chopper, and then the light irradiates on the target skin after passing corollary equipment such as a fiber. Wherein the wavelength range of the continuous light source can be 0.8~2.5 µm, while several wavelengths within or beyond the wavelength range of the continuous light source can be chosen as the discrete light source wavelength. While among the spectra overlapping range of the continuous light source and discrete light source, the measurement spectra can be the superposed spectra of the two kinds of spectra; it can also be only the spectra of discrete light source.

Switching of the composite light source can be conducted through light path switching or circuit switching controlled or uncontrolled by AOTF, wherein light path switching can be realized by using electrical signal to control electrical shutter, while circuit switch can be achieved by a spatial chopper or a computer.

In the present invention, optical sampling is achieved by a probe. Regarding the probe in such a non-invasive detection instrument, the continuous light source and discrete light source can be designed at the same position, and according to their light intensity the distribution mode of optical length is decided. They can also be placed in different positions, and according to their light intensity the distribution mode of optical length is decided.

In the present invention, the composite spectral method is implemented in the receiving unit. There are two ways for this method, that is, adding the continuous and discrete spectra overlapped or adding the continuous and discrete spectra non-overlapped. The first way refers to that measurement is performed in the overlapping range of these two spectra with these spectra being superposed. The second way means that in the overlapping range, spectra from only one path are chosen, or spectra from both paths are chosen respectively and measured separately.

For the composite spectral method in the present invention, the sequential control can be achieved in two ways: one is to separately measure the continuous spectra and discrete spectra, that is, first measure the continuous spectra, then the discrete spectra, or the discrete spectra first while the continuous spectra later; the other one is cross measurement, that is, the continuous spectra and discrete spectra are alternately measured in the order of wavelengths.

In practical use, the composite spectral method in the present invention can be exerted in the following four ways. The first one is that both the continuous light source and discrete light source are light-split by the AOTF. (FIG. 9 is an embodiment explaining this way.) In every measurement cycle, the AOTF starts first, and when the AOTF reaches the wavelength of each discrete light source, a D/A conversion card controls the AOTF to begin its special working mode (to change the sampling cycle under normal working condition into a special sampling cycle), and then the combined spectra are superposed and pass the AOTF. At the same time, the computer is notified and then it gives a control signal to select and start the photoelectric conversion and processing circuits with different gains, and then the AOTF returns to its normal working mode (the recovery of the sampling cycle under normal working condition). To eliminate thermal noise and make fine tuning more convenient, a shielded thermal equilibrium cover and fine tuning alignment device 15 are set in corresponding photoelectric conversion and processing circuits, which, in the present invention, can be photoelectric conversion and processing circuits 13, 14 and 18, whose gains are different from each other. Second, the AOTF conducts light-splitting for the continuous light source, whereas the discrete light source directly irradiates on the probe. (FIG. 10 is an embodiment explaining this way.) In every measurement cycle, the AOTF starts first, and when the AOTF reaches the wavelength of each discrete light source, a D/A conversion card controls the AOTF to begin its special working mode, and then the combined spectra are superposed and pass the AOTF. At the same time, the computer is notified and then it gives a control signal to select and start the corresponding photoelectric conversion and processing circuits 13, 14 and 18, and then the AOTF returns to its normal working mode. Third, the AOTF conducts light-splitting for the continuous light source, whereas the discrete light source directly irradiates on the probe. (FIG. 10 is an embodiment explaining this way.) In every measurement cycle, the AOTF starts first, and when the AOTF reaches the wavelength of each discrete light source, a D/A conversion card controls the AOTF to let the discrete spectra among the composite spectra pass, but prevent the continuous spectra from passing. At the same time, the computer is notified and then it gives a control signal to select and start the corresponding photoelectric conversion and processing circuits 13, 14 and 18, and then the AOTF returns to its normal working mode. Fourth, the AOTF conducts light-splitting for the continuous light source, whereas the discrete light source directly irradiates on the probe. (FIG. 11 is an embodiment explaining this way.) In every measurement cycle, the continuous light source controlled by the AOTF works first. When a cycle is completed, a D/A conversion card controls each discrete light source and enables it to begin work, and at the same time, the computer is notified and then it gives a control signal to select and start the corresponding photoelectric conversion and processing circuits 13, 14 and 18.

In the present invention, when applying composite spectra with high SNR on multi-variable mathematical processing, to achieve a measuring result with high accuracy, we can use principle component regression (short as PCR) method, partial least squares (short as PLS) method and so on for data processing.

The composite spectral measurement method is achieved via a composite light source comprising a continuous light source and a discrete light source. Such a method improves incident NIR light intensity, and also enhances and strengthens the output light intensity at a certain wavelength that carries useful information of the target component within a substance especially human body. It enables the spectral detection in the whole wavelength range with high accuracy, and thus comprehensively and significantly enhances the accuracy of the system for detecting component concentration.

Said composite spectral measurement method increases spectral measurement points that carry information of the target component within human body, and strengthens NIR light intensity at certain wavelength that carries useful information of the target component in human body.

Said composite spectral measurement method improves or strengthens the output light intensity at the wavelength that carries information of the target component within human body. It enables the spectral detection in the whole wavelength range, and thus significantly enhances the SNR of the detecting system.

DETAILED DESCRIPTION OF PREFERRED EMBODIMENTS

According the composite spectral measurement method mentioned above, we develop a non-invasive detection instrument for measuring certain component concentration within human tissue (for example, the blood glucose concentration). Further detailed description of the present invention is given as follows with respect to the following figures and embodiments.

Figure 1:
FIG. 1 is a graph showing an embodiment of a non-invasive instrument.
Figure 2:
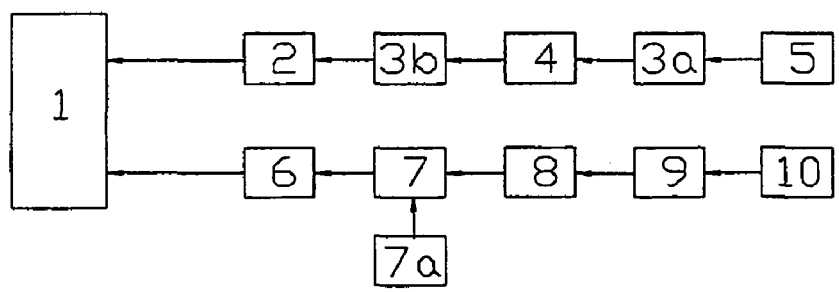
FIG. 2 shows a first embodiment of an incident unit in the non-invasive detection instrument.
Figure 3:
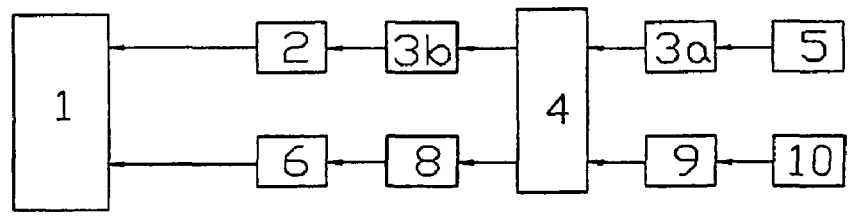
FIG. 3 shows a second embodiment of an incident unit in the non-invasive detection instrument.
Figure 4:
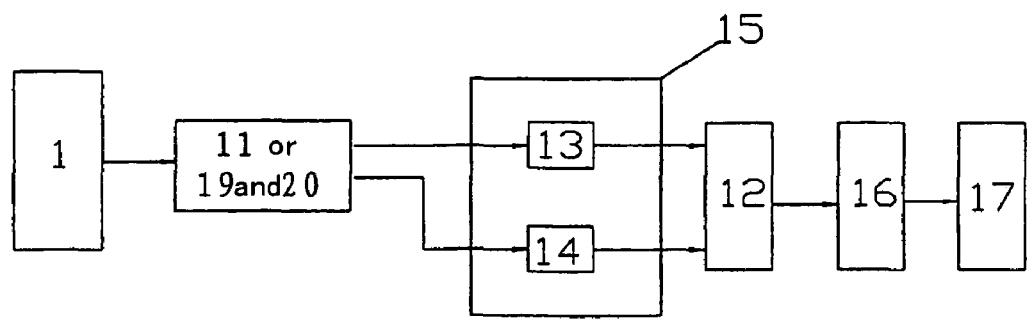
FIG. 4 shows a first embodiment of a receiving unit in the non-invasive detection instrument.
Figure 5:
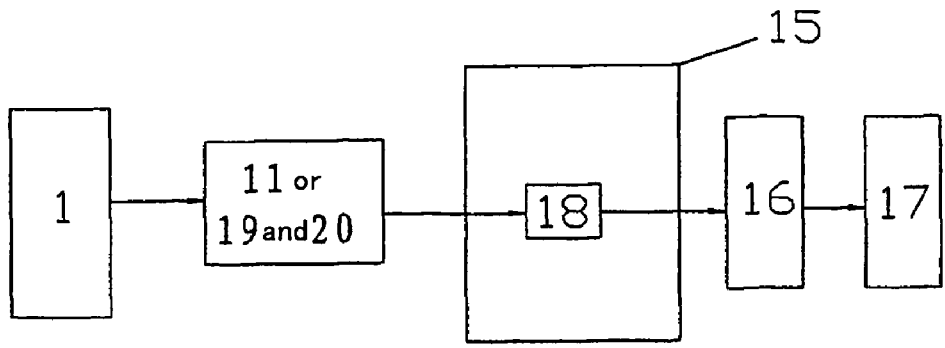
FIG. 5 shows a second embodiment of a receiving unit in the non-invasive detection instrument.

As shown in FIG. 1, the non-invasive detection instrument comprises of four modules, an incident unit 1a, a probe 1, a receiving unit 1b and a data processing unit 1c. Both of the schemes shown in FIG. 2 and FIG. 3 is suitable for said incident unit, and said receiving unit can be the one as shown in FIG. 4 or FIG. 5. The incident unit and receiving unit can be combined in an arbitrary way. Said data processing unit performs mathematical operation on the composite spectra achieved by said receiving unit, and thus, the concentration of the target component, for example, blood glucose, can be obtained.

Figure 8:
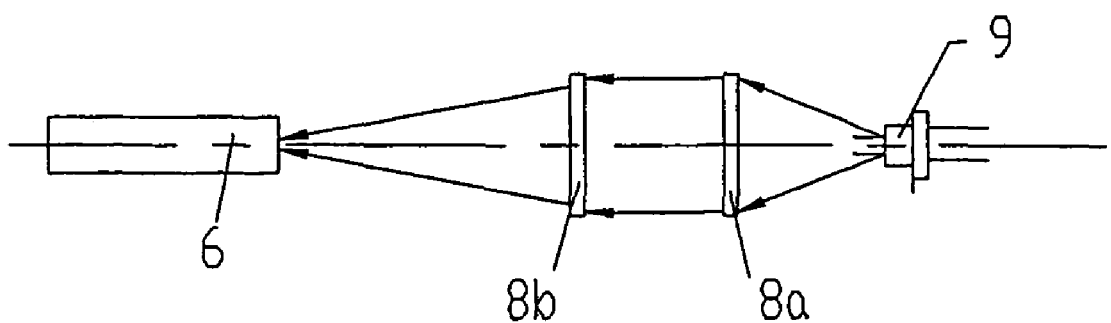
FIG. 8 shows an embodiment of the coupling between a discrete light source LD and a fiber.

FIG. 2 shows an embodiment of the incident unit 1a in the non-invasive detection instrument. The incident light path of the probe 1 comprises of an incident fiber 2 of the continuous light source and an incident fiber 6 of the discrete light source. The continuous light source 5 can be a tungsten halogen lamp, which is light-split by an AOTF crystal 4. The light path supplementary equipment 3a of said continuous light source includes a temperature control and processing device for the light source, a focusing lens, a light path channel and a prism, while the light path supplementary equipment 3b of said continuous light source includes a polarizing film, a focusing lens and so on. The discrete light source 9 can be one or several LDs of different wavelengths, for example, in blood glucose sensing, five LDs respectively corresponding to the wavelength 980 nm, 1310 nm, 1550 nm, 1610 nm and 1650 nm can be the discrete light source. The LD driving power supply 10 is a constant current source. Additionally, a set of focusing lens 8 (FIG. 8 gives an example for explaining a way to realize fiber coupling through a set of focusing lens) are used for coupling an LD with the transmission fiber 6 of the discrete light source, at the same time, an LD gating baffle 7 controlled by a spatial chopper 7a is chosen as a gating switch.

FIG. 3 shown another embodiment of the incident unit 1a in a non-invasive detection instrument. This method is basically similar to the one shown in FIG. 2, and the difference is in that the discrete light source is selectively light-split as the continuous light source is, and it does not use the LD gating baffle 7 controlled by a spatial chopper 7a as shown in FIG. 2 for light-splitting.

FIG. 4 and FIG. 5 are embodiments of the receiving unit.

FIG. 4 is a graph showing an embodiment of the receiving unit 1b in the non-invasive detection instrument. The receiving light path of the probe 1 is configured through the connection of a receiving fiber 11 (or 19) and 20 with the photoelectric conversion and processing circuit 13 and 14, respectively. Then, the control function of a controller 12 is achieved by a computer's choosing the output signal in corresponding channels of the photoelectric conversion and processing circuits 13 and 14. After being processed by a shielded thermal equilibrium cover and a fine tuning alignment device 15, the output signal is transferred to an NI terminal board or shielded joint 16, finally being processed by a computer 17.

FIG. 5 is a graph showing another embodiment of the receiving unit 1b in the non-invasive detection instrument. The receiving light path of the probe 1 is configured through the direct connection of a receiving fiber 11 (or 19) and 20 with a gain-tunable photoelectric conversion and processing circuit 18, and the light path does not go through the controller 12. Similar to FIG. 4, after being processed by a shielded thermal equilibrium cover and a fine tuning alignment device 15, the output signal is transferred to an NI terminal board or shielded joint 16, finally being processed by a computer 17.

Figure 6:
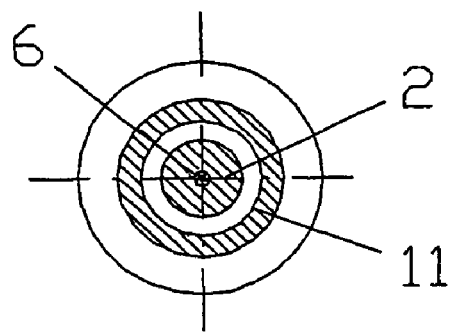
FIG. 6 shows a first embodiment of a fiber probe in the non-invasive detection instrument.
Figure 7:
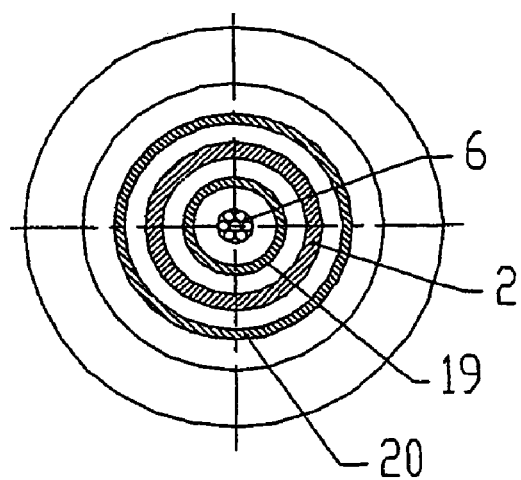
FIG. 7 shows a second embodiment of a fiber probe in the non-invasive detection instrument.

FIG. 6 and FIG. 7 are detailed embodiments of the probe.

FIG. 6 shows an embodiment of the probe 1 in the non-invasive detection instrument, where the continuous light source and discrete light source are placed at the same position. In the central position of the probe, a discrete light source transmission fiber 6 and a continuous light source transmission fiber 2 are placed.

A receiving fiber is provided in the external ring of the probe. Such a layout effectively concentrates the incident light intensity, and simultaneously prevents a majority of stray light that hasn't been scattered by deep tissue but only reflected by surface from being received.

FIG. 7 is another embodiment of the probe 1 in the non-invasive detection instrument, where the continuous light source and discrete light source are place at different positions. A discrete light source transmission is provided at the centre of the probe is fiber 6, an inner receiving fiber 19 is provided in its internal ring, an outer receiving fiber 20 is provided in its external ring, and a continuous light source transmission fiber 2 is provided in the middle ring. Such a layout utilizes the light intensity of the discrete light source thoroughly, where dispersed light irradiates on the target position, and internal and external light paths are used to receive the fully reflected light from the tissue, greatly increasing the intensity of detectable biological signals.

FIG. 8 shows an embodiment of the coupling between a discrete light source LD and a fiber in the incident unit 1a of a non-invasive detection instrument. Wherein, a discrete light source LD 9 is coupled with a discrete light source incident fiber 6 through a focusing lens 8a and another focusing lens 8b. Such a coupling method can enable the incident light intensity to be received by the fiber as much as possible.

Figures 1, 9:
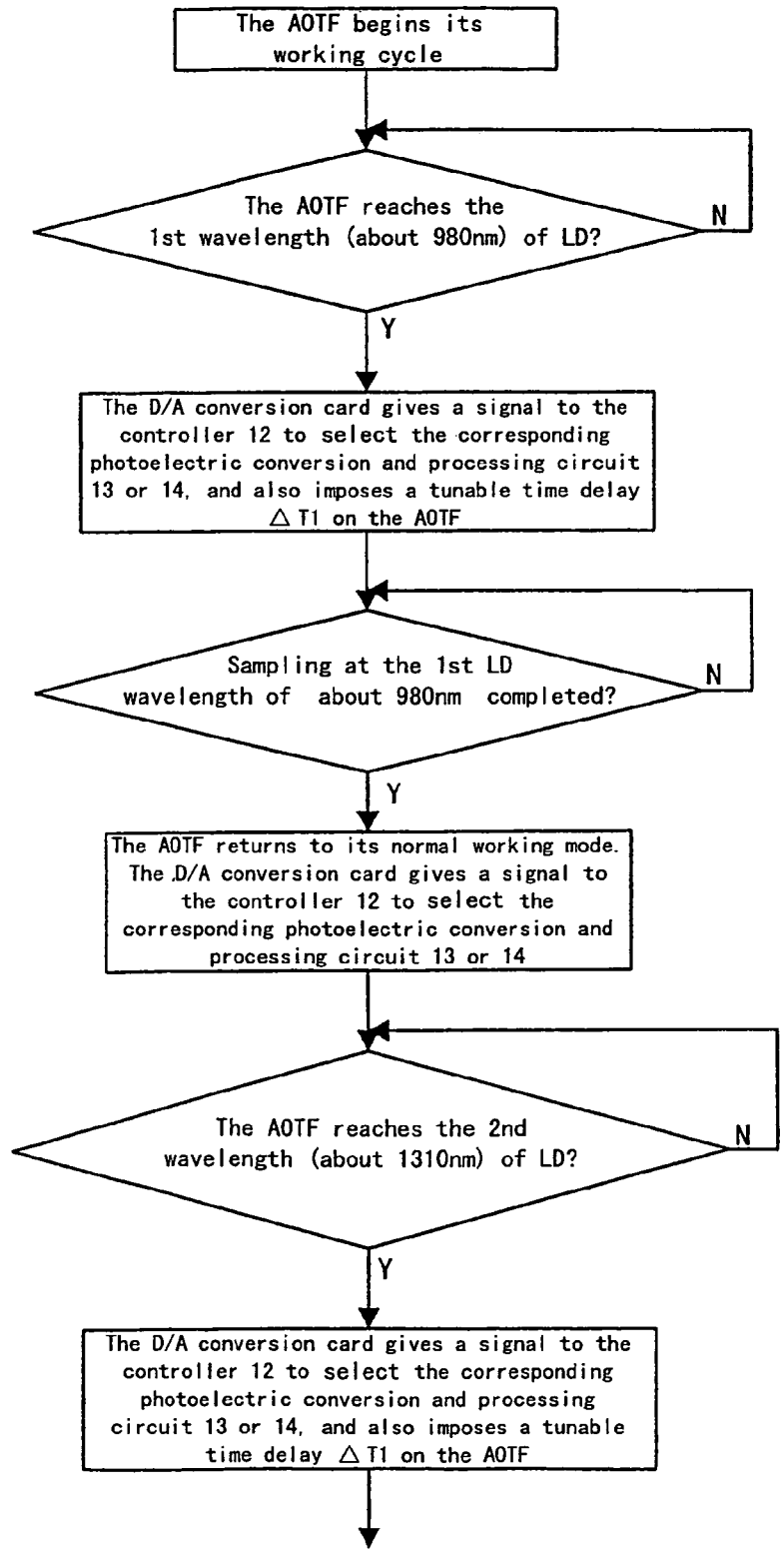
FIG. 9 (depicted as FIG. 9-1 through FIG. 9-4) is a flow diagram explaining the data acquisition after the light from continuous light source and discrete light source LD is conducted light-splitting by the AOTF and irradiates on the target position.
Figures 3, 9:
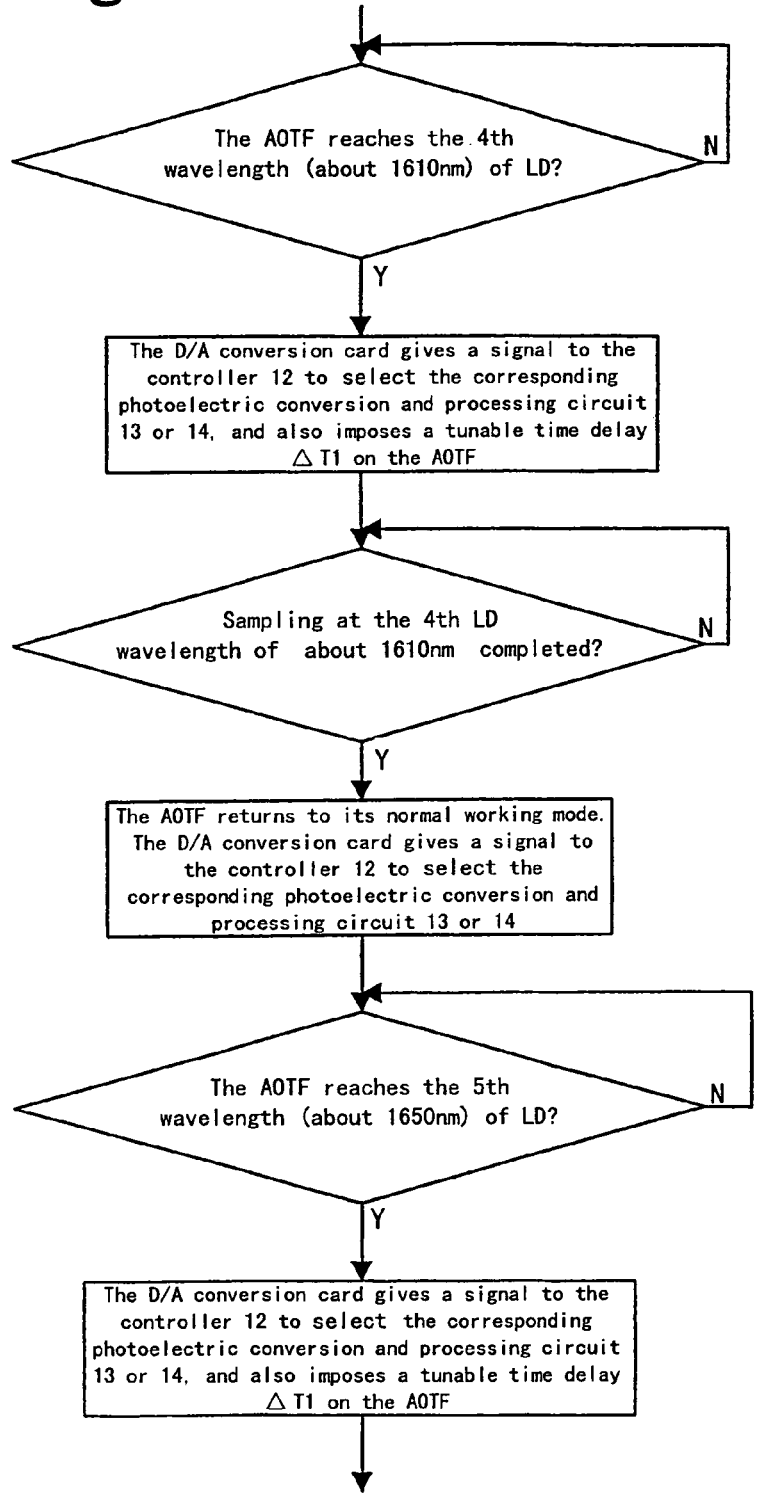
Figures 4, 9:
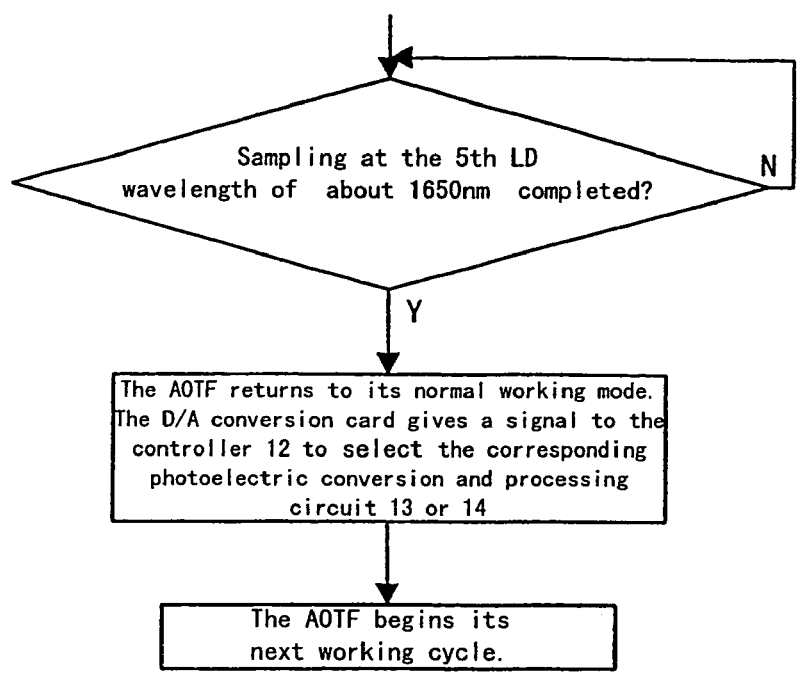
Figures 1, 10:
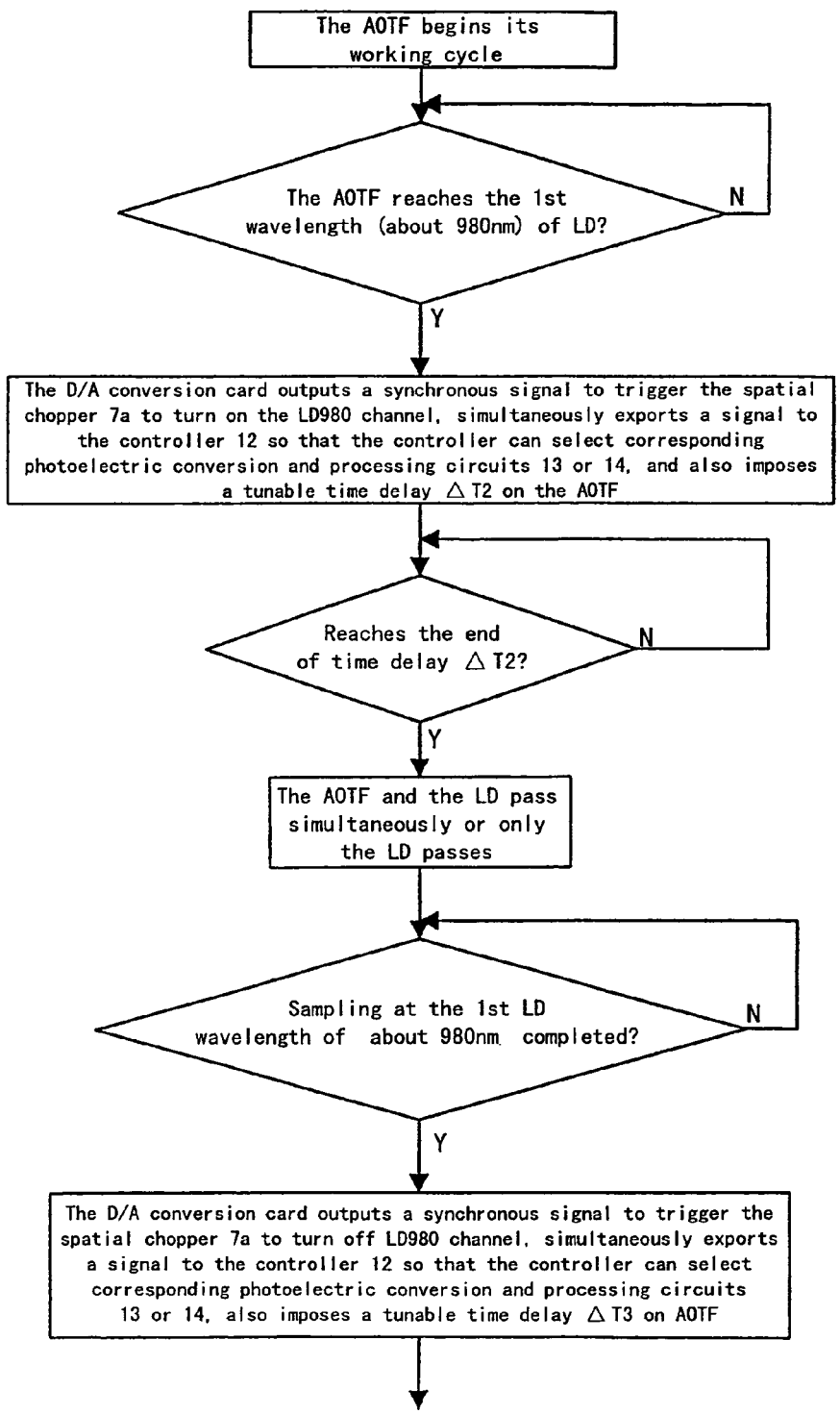
FIG. 10 (depicted as FIG. 10-1 through FIG. 10-4) is a flow diagram explaining the data acquisition after the light from continuous light source and light from discrete light source LD without light-splitting simultaneously irradiate on the target position.
Figures 2, 10:
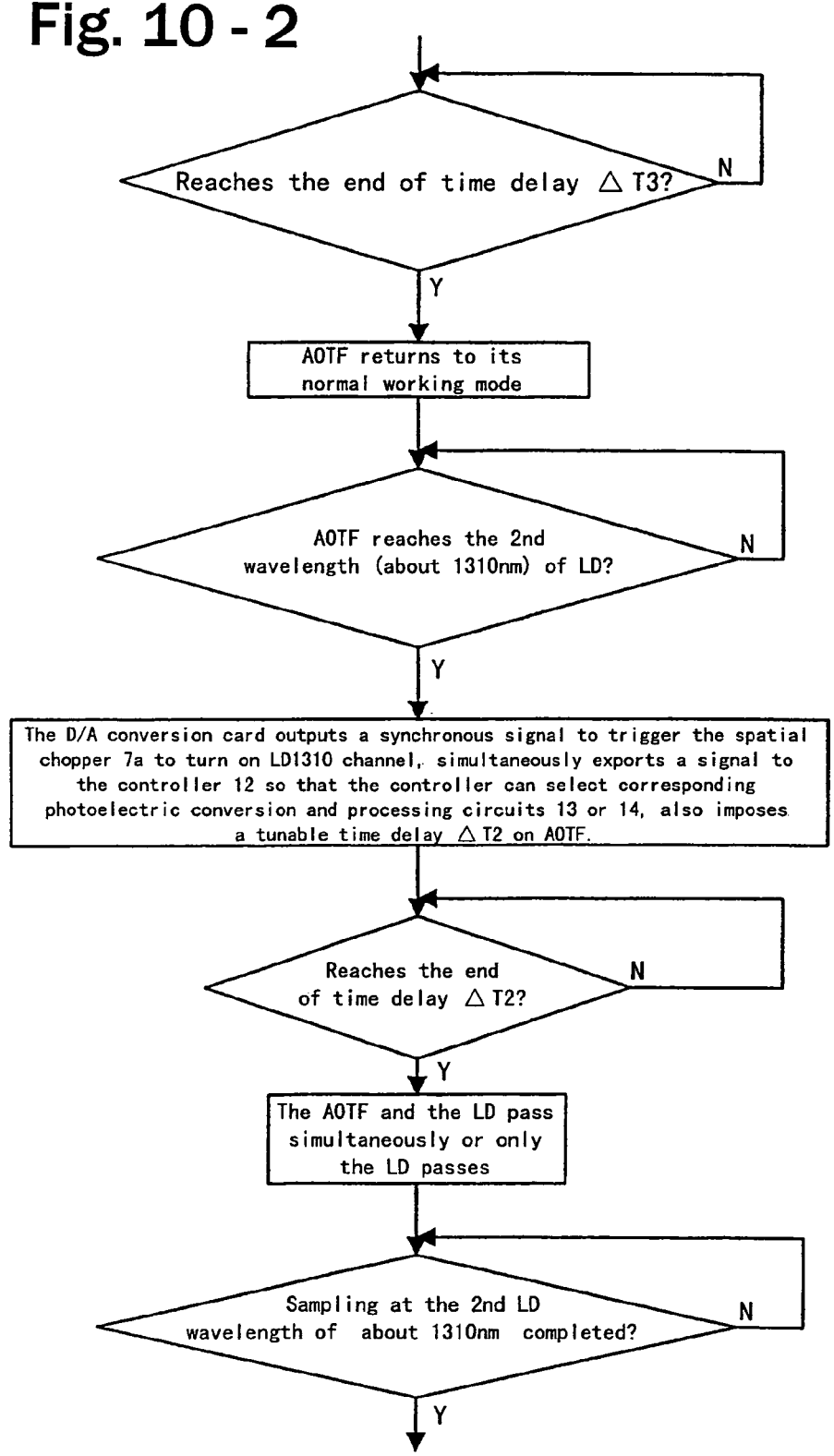
Figures 3, 10:
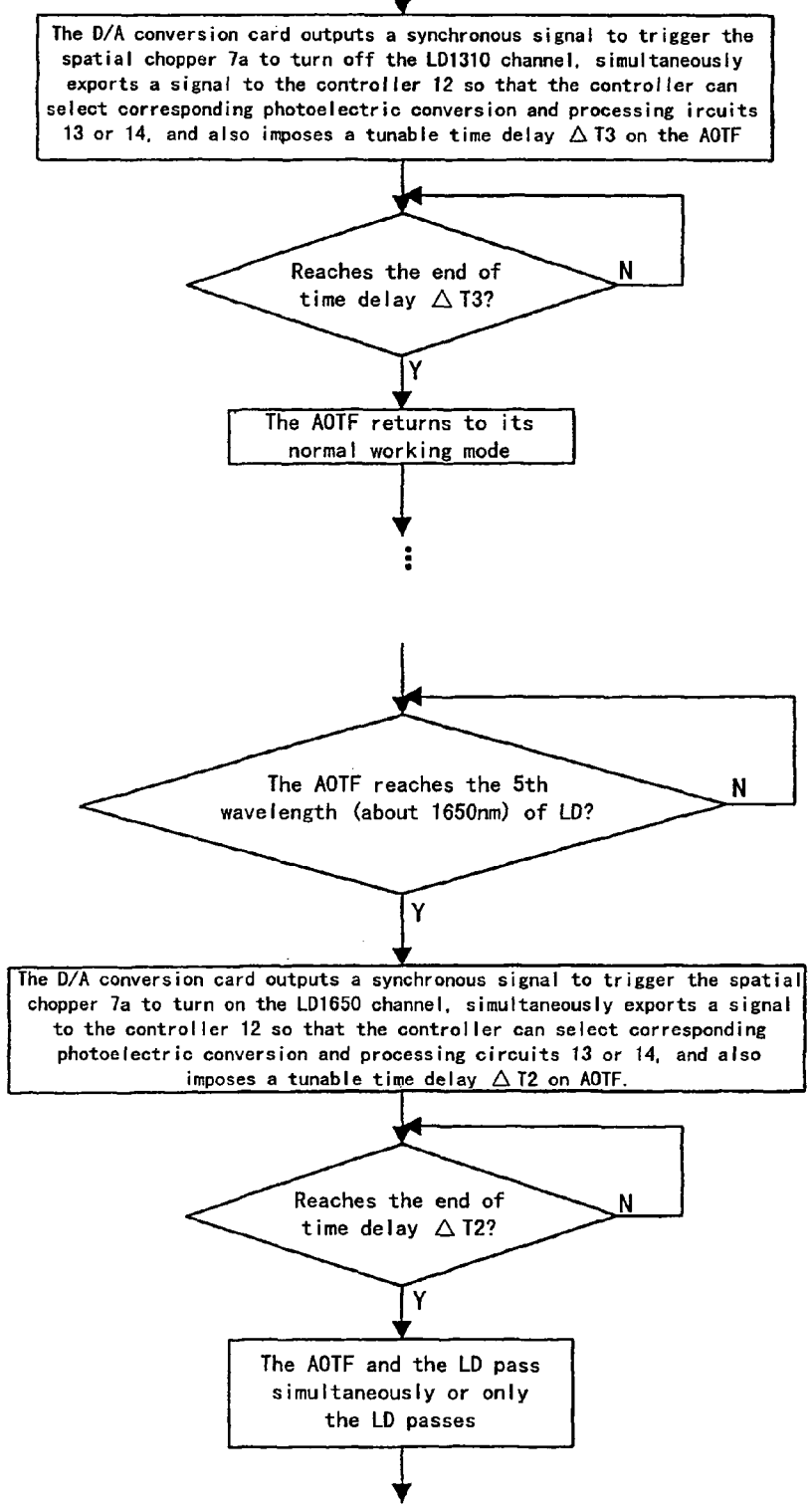
Figures 4, 10:
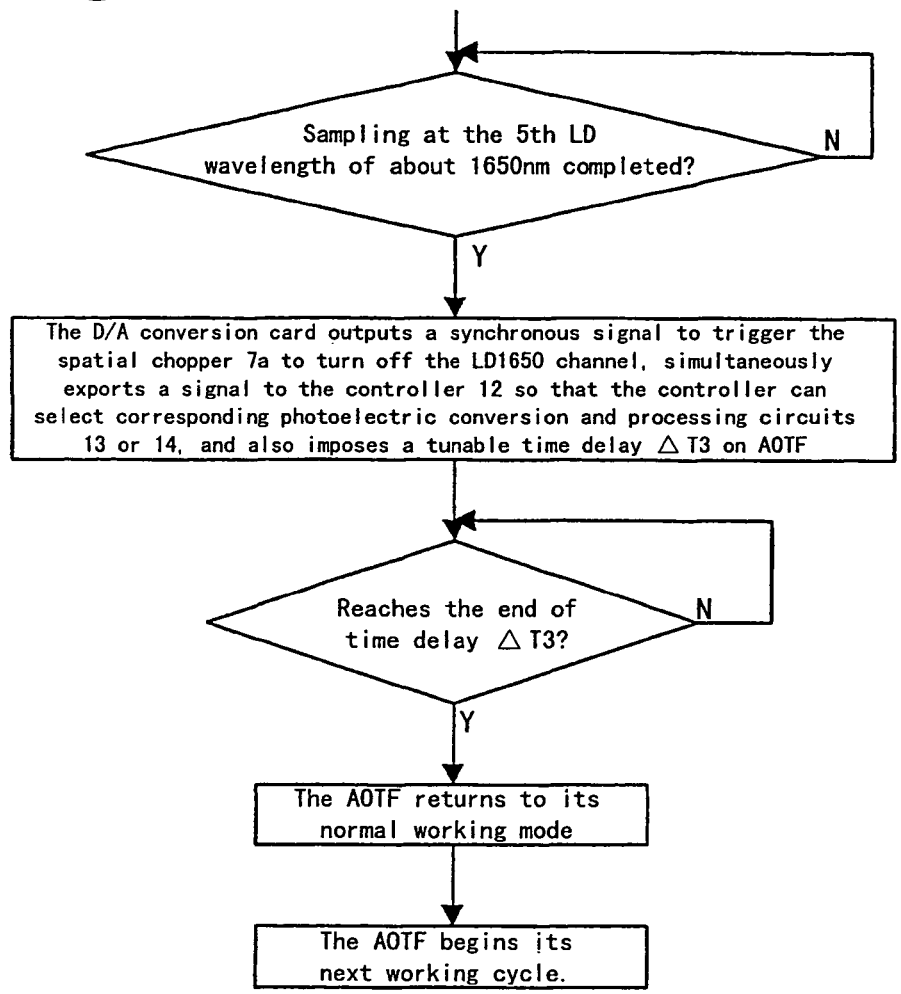
Figures 1, 11:
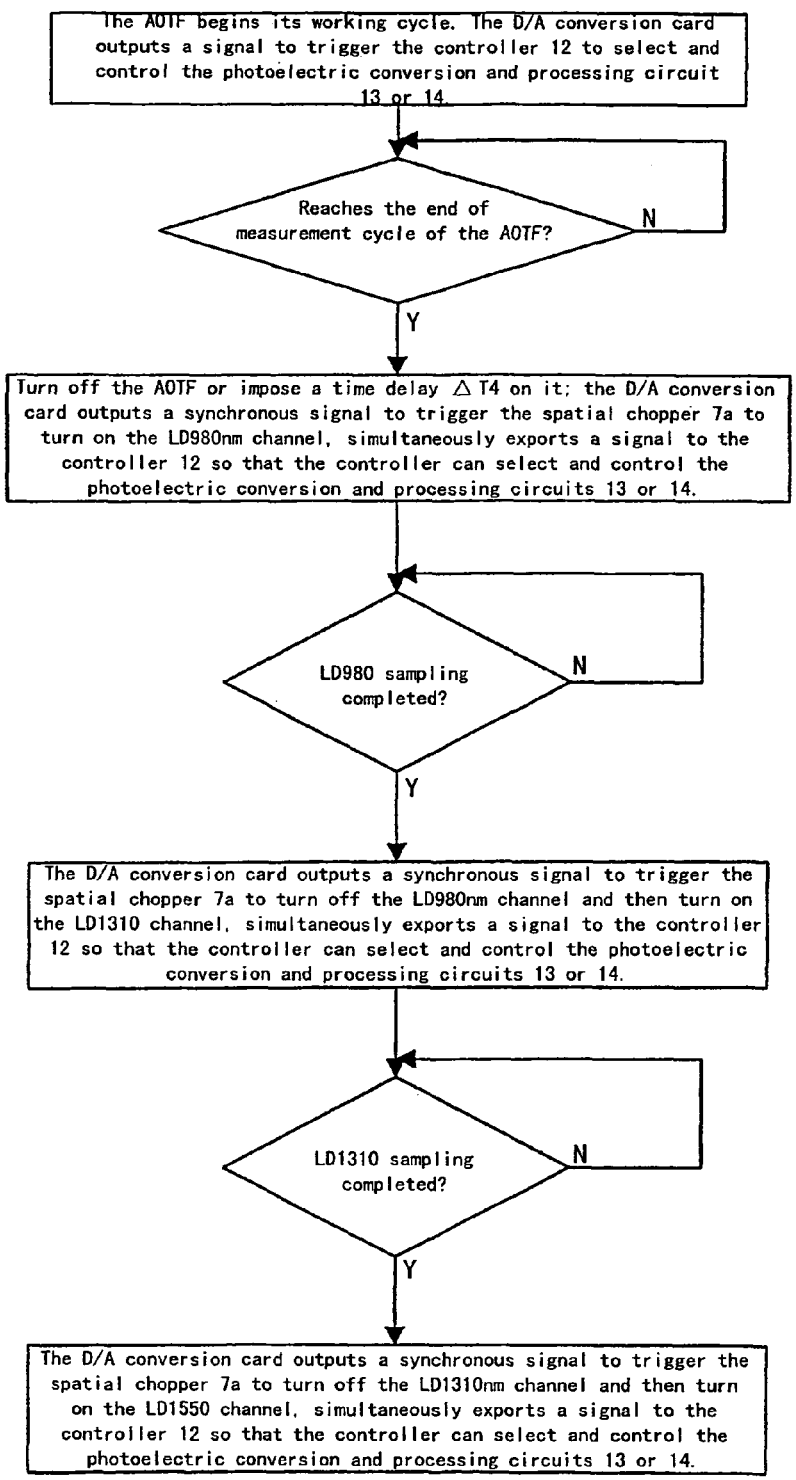
FIG. 11 (depicted as FIG. 11-1 through FIG. 11-2) is a flow diagram explaining the data acquisition after the light from continuous light source and light from discrete light source LD without light-splitting separately irradiate on the target position.
Figures 2, 11:
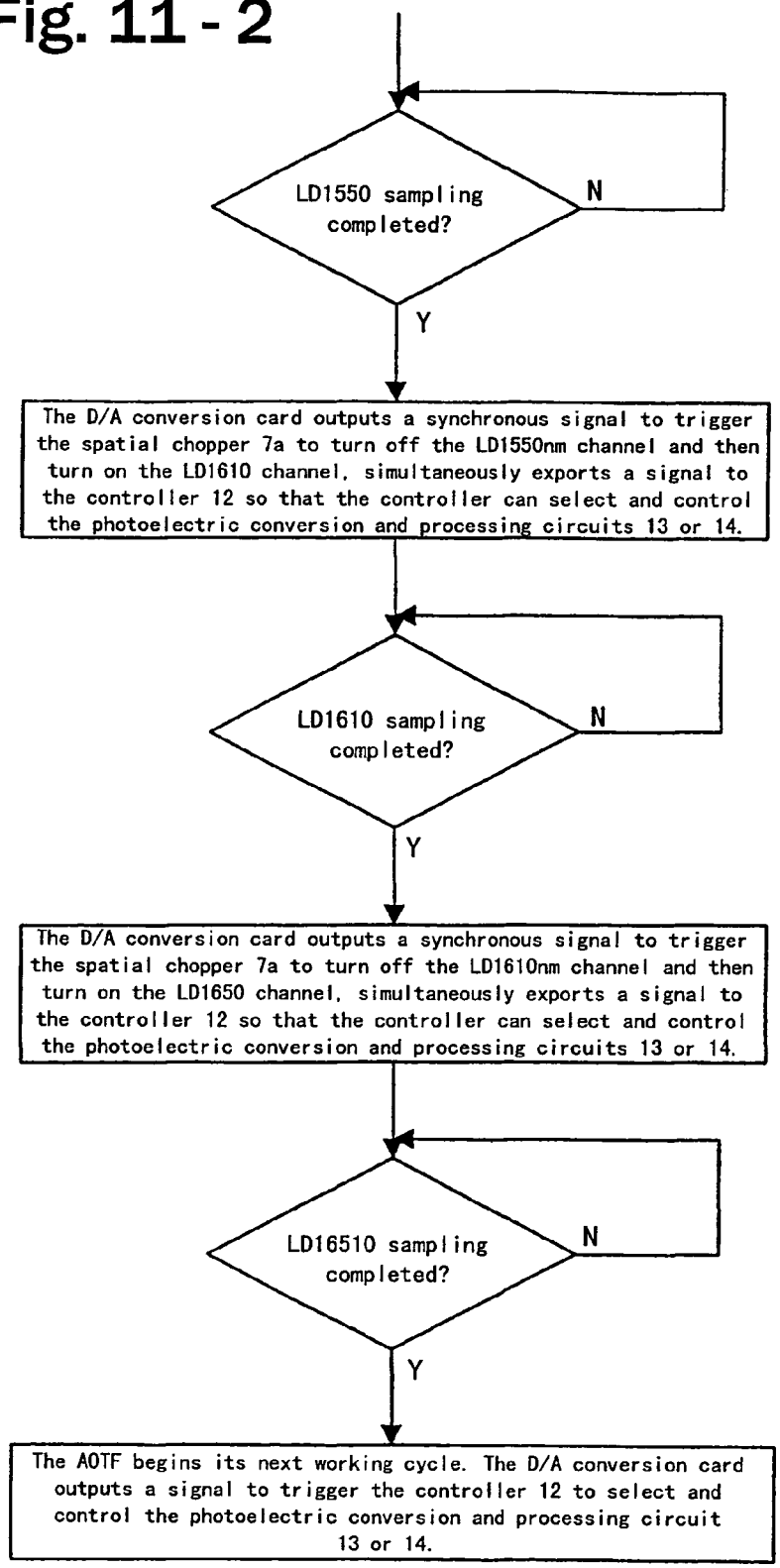

FIG. 9, FIG. 10 and FIG. 11 show three specific measurement methods.

FIG. 9 shows a processing method of the non-invasive detection instrument, a flow diagram explaining the data acquisition after the light from continuous light source and discrete light source LD is light-split by the AOTF and irradiates on the target position. Both the continuous light source and discrete light source have been light-split by the AOTF. In every measurement cycle, the AOTF starts first, and when the AOTF reaches the wavelength of each discrete light source (for example, the AOTF reaches the first wavelength 980 nm), a D/A conversion card controls the AOTF to begin its special working mode, that is, to impose a tunable time delay $\Delta T1$ on the AOTF so that both continuous spectra and discrete spectra are superposed and pass the AOTF simultaneously. At the same time, a controller 12 is given a signal by the D/A conversion card to turn on the corresponding photoelectric conversion and processing circuit 13 or 14, and then after the sampling at the wavelength (for example, the first wavelength of 980 nm) of the discrete light source is completed, the AOTF returns to its normal working mode and continues sequential acquisition process.

FIG. 10 shows a processing method of the non-invasive detection instrument. The AOTF conducts light-splitting for the continuous light source, whereas the discrete light source directly irradiates on the probe. In every measurement cycle, the AOTF starts first, and when the AOTF reaches the wavelength of each discrete light source (for example, the AOTF reaches the first wavelength 980 nm), a D/A conversion card controls the AOTF to begin its special working mode, that is, to impose a tunable time delay $\Delta T2$ on the AOTF; at the same time, the D/A conversion card outputs a synchronous signal to trigger a spatial chopper 7a so as to turn on corresponding channel of discrete light source (for example, a 980 nm laser), and simultaneously a signal is exported by the D/A conversion card to the controller 12 to turn on the corresponding photoelectric conversion and processing circuit 13 or 14. After time delay $\Delta T2$, the combined spectra are superposed and pass the AOTF (or only the discrete spectra among the composite spectra passes, while the continuous spectra are prevented), followed by sampling process. After the sampling at the wavelength (for example, the first wavelength of 980 nm) of the discrete light source is completed, the D/A conversion card imposes a tunable time delay $\Delta T3$ on the AOTF. Then, the D/A conversion card outputs a synchronous signal to trigger the spatial chopper 7a so as to turn off the corresponding channel of discrete light source (for example, the 980 nm laser). Simultaneously, a controller 12 is given a signal by the D/A conversion card to turn on the corresponding photoelectric conversion and processing circuit 13 or 14. After time delay $\Delta T3$, the AOTF returns to its normal working mode and continues sequential sampling process.

FIG. 11 shows a processing method of the non-invasive detection instrument. The AOTF conducts light-splitting for the continuous light source, whereas the discrete light source directly irradiates on the probe. In every measurement cycle, the continuous light source controlled by the AOTF starts first. A D/A conversion card outputs a signal to trigger a controller 12 to select and control the photoelectric conversion and processing circuit 13 or 14. At the end of one AOTF's working cycle, the D/A conversion card outputs a signal to turn off the AOTF (or imposes a time delay $\Delta T4$ on the AOTF), while at the same time, the D/A conversion card also outputs a synchronous signal to trigger a spatial chopper 7a so as to turn on a corresponding channel of the discrete light source (for example, a 980 nm laser), and then a signal is exported by the D/A conversion card to the controller 12 to select and control the photoelectric conversion and processing circuit 13 or 14 so as to turn on the corresponding photoelectric conversion and processing circuit 13 or 14 once each discrete light source begins to work. After the sampling at the wavelength (for example, the first wavelength of 980 nm) of the discrete light source is completed, the D/A conversion card outputs a synchronous signal to trigger the spatial chopper 7a so as to turn off the corresponding channel of the discrete light source (for example, the 980 nm laser) and then turn on the channel of a discrete light source at next wavelength (for example, a 1310 nm laser). Simultaneously, the controller 12 is given a signal by the D/A conversion card to turn on the corresponding photoelectric conversion and processing circuit 13 or 14. After measurement of all discrete light sources, the AOTF is resumed (or after its tunable time delay ΔT4) to begin next working cycle, and simultaneously the controller 12 is given a signal by the D/A conversion card to turn on the corresponding photoelectric conversion and processing circuit 13 or 14.

The invention claimed is:

1. A composite spectral measurement method comprising:
   emitting a composite light from an incident light source composed of a continuous light source and a discrete light source, the continuous light source emitting wideband continuous light, the discrete light source emitting at least one single-wavelength light or at least one narrowband continuous light, wherein the wavelength of the at least one single-wavelength light or the spectrum of the narrowband continuous light is within a range of the spectrum of the wideband continuous light;
   using a probe, irradiating the composite light onto a target position, and receiving light reflected by the target position at the probe, wherein the wideband continuous light and the at least one single-wavelength light or at least one narrowband continuous light are irradiated onto the target position through an exiting position in the probe, and the light reflected by the target position is received at a receiving position;
   in a receiving unit, adding the wideband continuous light reflected by the target position and the at least one single-wavelength light or at least one narrowband continuous light reflected by the target position in an overlapped or non-overlapped manner, to obtain a composite spectrum; and
   in a data processing unit, analyzing the obtained composite spectrum by using a mathematical model to obtain a concentration of a component of interest.

2. The composite spectral measurement method according to claim 1, wherein the wideband continuous light and the at least one single-wavelength light or at least one narrowband continuous light are irradiated onto the target position respectively through different exiting positions in the probe, and the light reflected by the target position is received at a plurality of receiving positions.

3. The composite spectral measurement method according to claim 1, wherein the continuous light source is an acoustic optical tunable filter NIR spectrometer; and
   the discrete light source is a light emitting diode (LED), or a laser diode (LD), or a tunable semiconductor laser.

4. The composite spectral measurement method according to claim 3, wherein the discrete light source is composed of one or more laser diodes (LDs).

5. The composite spectral measurement method according to claim 1, wherein the range of the spectrum of the wideband continuous light is any wavelength band within 0.8-2.5 μm.

6. The composite spectral measurement method according to claim 5, wherein the wavelength of the at least one single-wavelength light is one of 980 nm, 1310 nm, 1550 nm, 1610 nm and 1650 nm.

7. The composite spectral measurement method according to claim 6, wherein the component of interest is blood glucose.

8. The composite spectral measurement method according to claim 1, wherein in the receiving unit, the wideband continuous light reflected by the target position and the at least one single-wavelength light or at least one narrowband continuous light reflected by the target position are measured by a sampling sequential control, in which the sampling sequential control comprises one of:
   measuring the wideband continuous light reflected by the target position first, and then measuring the at least one single-wavelength light or at least one narrowband continuous light reflected by the target position; or
   measuring the at least one single-wavelength light or at least one narrowband continuous light reflected by the target position first, and then measuring the wideband continuous light reflected by the target position; or
   according to a sequence of wavelength, alternatively measuring the wideband continuous light reflected by the target position and the at least one single-wavelength light or at least one narrowband continuous light reflected by the target position.

9. A non-invasive composite spectral detection instrument comprising:
   an incident light source composed of a continuous light source and a discrete light source for emitting a composite light, the continuous light source emitting wideband continuous light, the discrete light source emitting at least one single-wavelength light or at least one narrowband continuous light, wherein the wavelength of the at least one single-wavelength light or the spectrum of the narrowband continuous light is within a range of the spectrum of the wideband continuous light;
   a continuous light transmission fiber for transmitting the wideband continuous light emitted from the continuous light source;
   a discrete light transmission fiber for transmitting the at least one single-wavelength light or at least one narrowband continuous light emitted from the discrete light source;
   a probe for irradiating the composite light onto a target position, and for receiving light reflected by the target position;
   a receiving fiber for transmitting the light reflected by the target position and received by the probe;
   a receiving unit for adding the wideband continuous light reflected by the target position and the at least one single-wavelength light or at least one narrowband continuous light reflected by the target position in a overlapped or non-overlapped manner, to obtain a composite spectrum; and
   a data processing unit for analyzing the obtained composite spectrum by using a mathematical model to obtain a concentration of a component of interest.

10. The non-invasive composite spectral detection instrument according to claim 9, wherein a light exiting end of the continuous light transmission fiber is of a ring shape, a light exiting end of the discrete light transmission fiber is of a circle shape, a light incident end of the receiving fiber is of a ring shape, an end of the probe is of a circle shape,
   the light exiting end of the continuous light transmission fiber, the light exiting end of the discrete light transmission fiber and the light incident end of the receiving fiber are concentrically arranged with a center at the center of the end of the probe, the light exiting end of the discrete light transmission fiber is located at the center of the end of the probe, the light exiting end of the continuous light transmission fiber is immediately adjacent to the light exiting end of the discrete light transmission fiber, and the light incident end of the receiving fiber is outside of the light exiting end of the continuous light transmission fiber.

11. The non-invasive composite spectral detection instrument according to claim 9, wherein the receiving fiber comprises an inner receiving fiber and an outer receiving fiber, a light exiting end of the continuous light transmission fiber is of a ring shape, a light exiting end of the discrete light transmission fiber is of a circle shape, a light incident end of the inner receiving fiber and a light incident end of the outer receiving fiber are both of a ring shape, an end of the probe is of a circle shape, the light exiting end of the continuous light transmission fiber, the light exiting end of the discrete light transmission fiber, the light incident end of the inner receiving fiber and the light incident end of the outer receiving fiber are concentrically arranged with a center at the center of the end of the probe, the light exiting end of the discrete light transmission fiber is located at the center of the end of the probe, the light incident end of the inner receiving fiber is outside of the light exiting end of the discrete light transmission fiber, the light exiting end of the continuous light transmission fiber is outside of the light incident end of the inner receiving fiber, and the light incident end of the outer receiving fiber is outside of the light exiting end of the continuous light transmission fiber.

12. The non-invasive composite spectral detection instrument according to claim 9, wherein the continuous light source is an acoustic optical tunable filter NIR spectrometer; and the discrete light source is a light emitting diode (LED), or a laser diode (LD), or a tunable semiconductor laser.

13. The non-invasive composite spectral detection instrument according to claim 12, wherein the discrete light source is composed of one or more laser diodes (LDs).

14. The non-invasive composite spectral detection instrument according to claim 9, wherein the continuous light source emits the wideband continuous light whose spectrum has a range of any wavelength band within 0.8-2.5 μm.

15. The non-invasive composite spectral detection instrument according to claim 14, wherein the discrete light source emits the at least one single-wavelength light at a wavelength of one of 980 nm, 1310 nm, 1550 nm, 1610 nm and 1650 nm.

16. The non-invasive composite spectral detection instrument according to claim 15, wherein the component of interest is blood glucose.

17. The non-invasive composite spectral detection instrument according to claim 9, wherein the receiving unit measures the wideband continuous light reflected by the target position and the at least one single-wavelength light or at least one narrowband continuous light reflected by the target position using a sequential sampling control, in which the sequential sampling control is adapted to perform one of:

measuring the wideband continuous light reflected by the target position first, and then measuring the at least one single-wavelength light or at least one narrowband continuous light reflected by the target position; or measuring the at least one single-wavelength light or at least one narrowband continuous light reflected by the target position first, and then measuring the wideband continuous light reflected by the target position; or according to a sequence of wavelength, alternatively measuring the wideband continuous light reflected by the target position and the at least one single-wavelength light or at least one narrowband continuous light reflected by the target position.

* * * * *